United States Patent [19]

Pechan et al.

[11] Patent Number: 5,650,445

[45] Date of Patent: Jul. 22, 1997

[54] DIPHENYLHEXENE COMPOSITION FOR USE IN TREATING LIVER CARCINOMA AND PSORIASIS

[76] Inventors: Reinhard Pechan, Elektrastr 36, D-81925 München; Manfred Metzler, Im Speitel 23, D-76229 Karlsruhe, both of Germany

[21] Appl. No.: 607,863

[22] Filed: Feb. 27, 1996

Related U.S. Application Data

[63] Continuation of PCT/EP94/02837 Aug. 26, 1994

[30] Foreign Application Priority Data

Aug. 27, 1993 [DE] Germany .......................... 43 28 965.7

[51] Int. Cl.$^6$ .................................................. A61K 31/015
[52] U.S. Cl. ................................................................ 514/764
[58] Field of Search ............................................ 514/764

[56] References Cited

FOREIGN PATENT DOCUMENTS

93/22262  11/1993  WIPO .

OTHER PUBLICATIONS

Chemische Berichte, vol. 115, No. 12, 1992, pp. 3697–3705, J. Leimner et al, "Stereochemie und Nebenprodukte der reduktiven . . . ".

*Primary Examiner*—Raymond Henley, III
*Attorney, Agent, or Firm*—Nikaido Marjelstein Murray & Oram LLP

[57] ABSTRACT

The new compound 3,4-diphenyl-3-hexene has valuable pharmaceutical properties and is suitable for the treatment of diseases that are associated with degenerate cell growth in particular for the treatment of liver cancer and psoriasis.

2 Claims, No Drawings

DIPHENYLHEXENE COMPOSITION FOR USE IN TREATING LIVER CARCINOMA AND PSORIASIS

This application is a continuation of PCT/EP94/02837, filed Aug. 26, 1994, and designating the United States.

The present invention concerns the new chemical compound diphenyl-3-hexene, a process for its production and its use as a therapeutic agent.

Numerous diseases in humans are due to an uncontrolled growth of body cells. This disorder in proliferation can lead to a benign degeneration such as psoriasis vulgaris in the case of keratinocytes or β-thalassaemia in the case of erythrocytes or even to a malignant degeneration such as in all forms of cancer.

The aim of cancer therapy is to completely destroy tumour cells or at least to significantly inhibit their growth. Apart from surgical procedures and radiation therapy, nowadays chemotherapeutic agents such as 5-fluorouracil, cytosine arabinoside etc. are also available for treating cancer patients. However, a disadvantage of using these chemotherapeutic agents is that they can also damage healthy regions of the organism in addition to the tumour cells. Therefore for many years a search has been made for less aggressive methods of treatment. Thus the application of Tamoxifen for mammal carcinomas has produced the first very promising results (Jordan, Antiestrogens in Cancer Treatment, in: Stoll, B. A., Endocrine Management of Cancer, Karger, Basel (1988), 57–65). However, hitherto it has not been possible to treat many cancer diseases (e.g. carcinoma of the colon and pancreatic carcinoma) with drugs to an adequate extent (Cohen et al., Colorectal Cancer, and Brennan et al., Cancer of the Pancreas in: DeVita, V. T., Helman, S. and Rosenberg, St. A., Cancer, Lippincott Co., 3rd Edition (1989).

Mistakes in the expression of so-called oncogenes such as myc or ras (Tabin et al., Nature, 300 (1982), 143–149) are considered to be one of the major causes of the development of cancer. The degree of DNA methylation is an important mechanism for regulating gene expression—also in the case of oncogenes (Doerfler, J. gen. Virol., 57 (1981) 1–20). Thus using ras and myc oncogenes as an example it was possible to demonstrate a hypomethylation in the expressed cancerogenic state (Feinberg et al., Biophys. Res. Comm., 111 (1983) 47–54; Cheah et al., J. Nat. Cancer Inst., 73, (1984), 1057–1061). In addition it is known that the growth as well as the correct somatic function of degenerate cells can be regulated by a specific control of DNA methylation. This was shown by Ley et al. (DNA methylation and globin gene expression in patients treated with 4-azacytidine, in: Globin Gene Expression and Hematopoietic Differentiation, Alan P. Liss, New York (1983), 457–474). A further direct relationship between the methylation of DNA and disorders in the central nervous system was found in HIV-positive patients (Keating et al., Lancet, 337 (1991) 935–939).

Moreover a direct relationship between malignant transformation and DNA hypomethylation on the one hand and between the concentration-dependent growth inhibition of tumour cells (from humans and animals) and DNA hypomethylation on the other hand was demonstrated in in vitro cell culture experiments (Pechan, (1987), Dissertation, University Würzburg).

An object of the present invention was to provide a new compound which exhibits a pharmaceutical efficacy in the treatment of diseases that are associated with degenerate cell growth i.e. disorders in cell proliferation.

The object according to the invention is achieved by 3,4-diphenyl-3-hexene.

The compound according to the invention can be obtained by a process which is characterized in that 1-phenyl-1-propanone is reacted in the presence of a transition metal chloride, zinc dust and a base in an inert solvent and the desired compound is isolated from the reaction mixture by purification.

The transition metal chloride is preferably titanium tetrachloride and the base is preferably pyridine. The inert solvent is preferably 1,4-dioxane and the reaction is advantageously carried out at the reflux temperature of the solvent. Further details of this process are described in a publication by McMurry (J. Org. Chem. 54 (1989), 3748–3749).

Surprisingly the substance according to the invention significantly inhibits the growth of tumour cells in vitro. Therefore it would be expected that the compound is suitable as a therapeutic agent for the treatment of diseases that are associated with degenerate cell growth.

The present invention therefore also concerns a pharmaceutical composition which contains the compound according to the invention as an active substance and if desired common pharmaceutical carriers, fillers, diluents or/and auxiliary agents.

The compound according to the invention is suitable for all areas of indications in human and veterinary medicine in which DNA hypermethylation can inhibit the growth of or/and influence degenerate body cells. Particular examples are cancer, psoriasis or AIDS.

The pharmaceutical composition according to the invention can in this connection be administered in any desired formulations which contain the compound according to the invention. Examples of suitable formulations are tablets, capsules, granulates, solutions, ointments or aerosols. The production of such formulations is adequately well-known to a person skilled in the field of pharmacy so that a detailed description does not appear to be necessary.

The following example further elucidates the invention.

EXAMPLE 1

Synthesis of 3,4-diphenyl-3-hexene according to McMurry (1989, supra)

108 mmol titanium tetrachloride is added dropwise to 200 ml 1,4-dioxane while stirring (cooling on ice, argon atmosphere). 200 ml zinc dust and 8 ml pyridine are added in small portions to this solution. After the slow (30 min) addition of 1-(4-alkylphenyl)-1-propanone the reaction solution is heated under reflux (20 h). After cooling, this solution is admixed with 200 ml 10% potassium carbonate solution. The suspension formed in this manner is shaken with 50 ml diethyl ether, washed with water and dried over magnesium sulphate.

For purification the crude product is filtered over silica gel using petroleum ether/diethyl ether (4/1) and subsequently separated by column chromatography (silica gel, petroleum ether/diethyl ether 2/1). The pure substance (colourless) crystallizes in the cold after several days.

3,4-diphenyl-3-hexene

Yield: 27%

Melting point: 72.2° C.

EXAMPLE 2

Growth inhibition of tumour cells in vitro $10^4$ to $10^5$ tumour cells in 3 ml IBR medium in each case (15% foetal calf serum, 25 U/ml penicillin-streptomycin)

were sown in cell culture flasks (T25, Greiner). After a growth phase of 4 h (37° C., 12% $CO_2$) 50 µM test substance dissolved in 0.1% DMSO and 0.1% DMSO (control) were added. The compound of example 1 was used as the test substance.

The cells were counted (Neubauer counting chamber) at intervals of 24 h over a period of 9 days. The medium was changed after 3 and 6 days and the test substance (see example 1) was again added at the same concentration.

It was possible to inhibit the growth of HT29 liver carcinoma cells (human) by up to 90% in a concentration-dependent manner and that of in vitro transformed hamster cells by about 30%.

I claim:

1. A pharmaceutical composition comprising 3,4-diphenyl-3-hexene and one or more pharmaceutically acceptable carriers, fillers, diluents and/or auxilliary substances.

2. A method for treating a disease that is associated with degenerate cell growth, wherein the disease is selected from the group consisting of liver carcinoma and psoriasis, in a patient in need of such treatment, comprising administering to the patient a disease-treating effective amount of 3,4-diphenyl-3-hexene.

* * * * *